(12) United States Patent
Rubin

(10) Patent No.: US 6,238,699 B1
(45) Date of Patent: May 29, 2001

(54) PHARMACEUTICAL FORMULATIONS CONTAINING A COMBINATION OF CARBIDOPA AND LEVIDOPA

(76) Inventor: Alan A. Rubin, 207 Hitching Post Dr., Wilmington, DE (US) 19803

( * ) Notice: Subject to any disclaimer, the term of this patent is extended or adjusted under 35 U.S.C. 154(b) by 0 days.

(21) Appl. No.: 09/638,407

(22) Filed: Aug. 15, 2000

Related U.S. Application Data

(62) Division of application No. 08/835,482, filed on Apr. 8, 1997.

(51) Int. Cl.⁷ ............................... A61K 9/24; A61K 9/22
(52) U.S. Cl. ........................ 424/472; 424/464; 424/468
(58) Field of Search ................................. 424/464, 468, 424/472, 451, 457, 458, 459, 461

(56) References Cited

U.S. PATENT DOCUMENTS 4,900,755  2/1990  Dempski et al. ................. 424/469
5,738,874  *  4/1998  Conte et al. .

OTHER PUBLICATIONS

Various, Oral Solid Dosage Forms, *Remington's Pharmaceutical Sciences*, 17th Edition, Chapter 90, 1985.
Various, Coating of Pharmaceutical Dosage Forms, *Remington's Pharmaceutical Sciences*, 17th Edition, 1633, 1985.
Mark A. Longer and Joseph R. Robinson, PhD, Sustained–Release Drug Delivery Systems, *Remington's Pharmaceutical Sciences*, 17th Edition, 1644, 1985.
Various, Sinemet CR, *Physician' Desk Reference*,976, 1993.
Various, Drugs for Parkinson's Disease *The Medicl Letter on Drugs and therapeutics*, 35 (Issue 894), 31–34, Apr. 16, 1993.
Ahlskog, J. Eric, MD, PhD, Parkinson's Disease: Update on Pharmacologic Options to Slow Progression and Treat Symptons, *Hosp. Formul.*, 27, 146–152, 161–163, Feb. 1992.

* cited by examiner

*Primary Examiner*—Thurman K. Page
*Assistant Examiner*—Brian Seidlech
(74) *Attorney, Agent, or Firm*—Gildo E. Fato

(57) ABSTRACT

An oral anti-Parkinson drug delivery system consisting of carbidopa and levodopa in immediate and sustained release compartments provides a significant clinical advantage over currently available carbidopa-levodopa preparations.

1 Claim, No Drawings

PHARMACEUTICAL FORMULATIONS CONTAINING A COMBINATION OF CARBIDOPA AND LEVIDOPA

This is a division of application Ser. No. 08/835,482 filed Apr. 8, 1997.

BACKGROUND OF THE INVENTION

1. Field of the Invention

This invention relates to an improvement in the treatment of Parkinson's disease and related disorders. More specifically, the present invention introduces novel formulations of the combination carbidopa and levodopa, the current mainstay of therapy.

2. Background and Prior Art

Parkinson's disease is associated with the depletion of dopamine from cells in the corpus striatum. Since dopamine does not cross the blood brain barrier and cannot therefore be used to treat Parkinson's disease, its immediate precursor, levodopa, is used instead because it penetrates the brain where it is decarboxylated to dopamine. But levodopa is also decarboxylated to dopamine in peripheral tissues and consequently only a small portion of administered levodopa is transported unchanged to the brain. This reaction can be blocked by carbidopa which inhibits decarboxylation of peripheral levodopa but cannot itself cross the blood brain barrier and has no effect on the metabolism of levodopa in the brain.

The combination of carbidopa and levodopa is considered to be the most effective treatment for symptoms of Parkinson's disease (The Medical Letter, 35:31–34, 1993). Nevertheless, certain limitations become apparent within two to five years of initiating combination therapy. As the disease progresses, the benefit from each dose becomes shorter ("the wearing off effect") and some patients fluctuate unpredictably between mobility and immobility ("the on-off effect"). "On" periods are usually associated with high plasma levodopa concentrations and often include abnormal involuntary movements, i.e., dyskinesias. "Off" periods have been correlated with low plasma levodopa and bradykinetic episodes.

In an effort to reduce the occurrences of "wearing off" and "on-off" phenomena, a controlled release oral dosage combination was introduced with claims of slow and simultaneous release of carbidopa and levodopa from the formulation (U.S. Pat. No. 4,900,755 issued Feb. 13, 1990). Data from clinical trials cited in the patent indicate that effective anti-Parkinson effects were achieved with fewer daily doses of the controlled release form as compared with the conventional combination.

Nevertheless, there remains a significant flaw in the therapeutic application of controlled release carbidopa-levodopa; that is, the considerable delay in onset of action. Mean time to peak concentration in healthy elderly subjects was found to be two hours for controlled release carbidopa-levodopa and only 0.5 hours for the conventional form (Physicians Desk Ref., 47th Ed., p. 976, 1993). A controlled release dosage form that could also provide rapid onset of action, at least equivalent to that of conventional carbidopa-levodopa would have an obvious clinical advantage over current therapy.

The strategy proposed in the present invention is to formulate oral dosage forms containing both immediate release carbidopa-levodopa and controlled release carbidopa-levodopa. Ingestion would provide rapid onset anti-Parkinson activity via the immediate release component followed by sustained therapeutic activity from the controlled release component.

SUMMARY OF THE INVENTION

It is the purpose and principal object of this invention to provide an improved method for the treatment of Parkinson's disease by using novel formulations of the combination carbidopa-levodopa which a) are effective in preventing the symptoms of Parkinson's disease and yet which b) act rapidly, avoiding significant onset delay common to the standard controlled release therapy.

DETAILED DESCRIPTION

The novel oral dosage formulations of the present invention each contain immediate release and controlled release components of the anti-Parkinson agents carbidopa (5–200 mg) and levodopa (25–600 mg). The conventional immediate release combination of carbidopa-levodopa reaches peak plasma concentrations in 30 minutes, whereas the onset of the controlled release component is two hours followed by prolonged release over a four- to six-hour period.

The usual daily therapeutic dose of levodopa, when administered with carbidopa, is 300 to 750 mg and the dose of carbidopa approximately 75 mg per day but the latter is apparently devoid of adverse effects even at doses of 400 mg per day (J. E. Ahlskog, Hosp. Form., 27:146, 1992). Although the optimum daily dosage of carbidopa-levodopa must ultimately be determined by titrating each patient, a preferred range for twice daily maintenance therapy may include immediate release of 10–25 mg carbidopa and 50–200 mg levodopa and sustained release of 25–75 mg carbidopa and 100–400 mg levodopa.

Specific examples of these formulations are cited below. The amount and excipients listed can be changed through methods known to those skilled in the preparation of immediate and sustained release dosage forms. Some of these methods are available in Remington's Pharmaceutical Sciences, $17^{th}$ Ed., 1985, a standard reference in the field.

EXAMPLE 1

A two compartment tablet consisting of a core layer of sustained release carbidopa-levodopa overcoated with a layer of immediate release carbidopa-levodopa. The core ingredients are blended separately (as are the outer layer ingredients), compressed to produce core tablets and then overcoated with the compressed outer layer blend using a suitable coating press.

| Ingredient | Mg per Tablet |
| --- | --- |
| Outer Layer (Immediate Release) | |
| Carbidopa | 25.0 |
| Levodopa | 100.0 |
| Microcrystalline Cellulose | 224.0 |
| Croscarmellose Sodium | 15.0 |
| Silicon Dioxide | 3.0 |
| Magnesium Stearate | 3.0 |
| Core Layer (Sustained Release) | |
| Carbidopa | 50.0 |
| Levodopa | 200.0 |
| Methocel E4M Premium CR | 80.0 |
| Microcrystalline Cellulose | 61.0 |

-continued

| Ingredient | Mg per Tablet |
|---|---|
| Croscarmellose Sodium | 15.0 |
| Silicon Dioxide | 2.0 |
| Magnesium Stearate | 2.0 |

EXAMPLE 2

A bilayer or multilayer tablet consisting of one layer of sustained release carbidopa-levodopa either adjacent to a layer of immediate release carbidopa-levodopa or separated by an additional excipient layer. The ingredients from each layer are blended separately, then compressed to produce a layered tablet using a suitable layered press.

| Ingredient | Mg per Tablet |
|---|---|
| Layer 1 (Immediate Release) | |
| Carbidopa | 12.5 |
| Levodopa | 50.0 |
| Microcrystalline Cellulose | 123.5 |
| Silicon Dioxide | 2.0 |
| Magnesium Stearate | 10.0 |
| Layer 2 (Sustained Release) | |
| Carbidopa | 37.5 |
| Levodopa | 150.0 |
| Methocel E4M Premium CR | 80.0 |
| Microcrystalline Cellulose | 53.5 |
| Silicon Dioxide | 2.0 |
| Magnesium Stearate | 2.0 |

EXAMPLE 3

An oral dosage form, such as a capsule or compressed tablet, containing immediate and sustained release carbidopa-levodopa pellets prepared by the following methods:

1. Dissolve Povidone in isopropyl alcohol (10% w/w)
2. Disperse micronized carbidopa and levodopa in Povidone solution
3. Layer the slurry from step 2 onto sugar spheres to form core pellets using a fluid-bed with a Wurster air suspension coating column
4. Dissolve ethyl cellulose and polyethylene glycol 4000 in methylene chloride and methanol (4:1) mixture (5% w/w)
5. Coat pellets from step 3 with polymer solution from step 4 in a fluid-bed with a Wurster air suspension coating column.

Appropriate amounts of uncoated core pellets containing immediate release carbidopa-levodopa (step 3) and polymer coated pellets containing sustained release carbidopa-levodopa (step 5) are included in an oral dosage form to provide the desired ratio of immediate and sustained release carbidopa-levodopa.

| Ingredient | Mg per Tablet |
|---|---|
| Uncoated Core Pellets (Immediate Release) | |
| Carbidopa | 12.5 |
| Levodopa | 50.0 |
| Povidone (K-30) | 17.5 |
| Sugar Spheres (35-40 Mesh) | 20.0 |
| Coated Pellets (Sustained Release) | |
| Core Pellet | 94.0 |
| Ethyl Cellulose | 4.5 |
| Polyethylene Glycol 4000 | 1.5 |

What is claimed is:

1. A pharmaceutical tablet for treating Parkinson's disease comprising a sustained release core layer of 25–75 mg of carbidopa, 100–400 mg of levodopa, 80 mg of a cellulose ether, and microcrystalline cellulose, wherein the sustained release layer is overcoated with an immediate release layer comprising 10–25 mg of of carbidopa and 50–200 mg of levodopa, wherein the sustained and immediate release layers are separated by a drug free exipient layer.

* * * * *